United States Patent [19]

Engleman et al.

[11] Patent Number: 4,950,598
[45] Date of Patent: Aug. 21, 1990

[54] PROCESS FOR MAKING T CELL HYBRIDOMAS

[75] Inventors: Edgar G. Engleman, Atherton; James W. Larrick, Woodside; Andrew A. Raubitschek, Palo Alto; Steven K. Foung, San Francisco, all of Calif.

[73] Assignees: The Board of Trustees of the Leland Stanford Junior University, Stanford; Cetus Corporation, Emeryville, both of Calif.

[21] Appl. No.: 777,947

[22] Filed: Sep. 19, 1985

Related U.S. Application Data

[63] Continuation of Ser. No. 421,060, Sep. 22, 1982, abandoned, which is a continuation-in-part of Ser. No. 376,191, May 7, 1982, abandoned.

[51] Int. Cl.$^5$ .................... C12N 15/00; C12N 5/00; C12N 5/02
[52] U.S. Cl. .................... 435/172.2; 435/70.2; 435/240.2; 435/240.21; 435/240.25; 435/240.26; 435/240.31; 530/351; 530/412; 530/809; 935/101; 935/93; 935/95
[58] Field of Search .................... 435/68, 172.2, 240, 435/26, 948, 240.27, 240.2, 240.1; 935/90, 101, 109

[56] References Cited

U.S. PATENT DOCUMENTS

| | | | |
|---|---|---|---|
| 4,350,683 | 9/1982 | Galfré et al. | 435/240 |
| 4,364,937 | 12/1982 | Kung et al. | 435/240 |
| 4,411,993 | 10/1983 | Gillis | 435/68 |
| 4,473,642 | 9/1984 | Gillis | 435/68 |
| 4,490,289 | 12/1984 | Stern | 260/112 R |

OTHER PUBLICATIONS

Gillis et al., J. Exp. Med., 152, 1709-19, (1980).
Harwell et al., J. Exp. Med., 152, 893 (1980).
Kamatani et al., PNAS (U.S.A.), 78(2), 1219-23, (Feb. 1981).
Lakow, E. et al., J. Cell. Biochem. Suppl., No. 6, p. 77 (1982). Oral Disclosure 2/28-3/5, 1982, Bio. Abs. 27010783.
Lakow, E. et al., Fed. Proc., vol. 41 (3), abs. 1919 (1982), Oral Disclosure of Apr. 15-23, 1982, Bio. Abs. 23044014J.
Cox, R. et al., Mutation Res., vol. 36(1), pp. 93-103 (1976), Bio. Abs. 62060609.
Pawalec, G. et al., Eur. J. Immunol., vol. 12(5), pp. 387-392. Bio. Abs. 75010764.
Gillis, S. et al., J. Exp. Med., vol. 152 (6), pp. 1709-1719 (1980). Bios. Abst. 71059830.
Frank, M. B. et al., J. of Immunology, vol. 127 (6), pp. 2361-2365 (1981). Bio. Abst. 74011171.
Irigoyen, O. et al., J. Exp. Med., vol. 154, pp. 1827-1837, (1981), "Generation of Functional Human T Cell Hybrids".
Chemical Abstracts, vol. 98, abstract no. 105727 w, 1983, Yamamura, Y. et al., "Human T-Cell Lines." (12 Jun. 1981).
Chemical Abstracts, vol. 98, abstract no. 874043, 1983, Kishimoto, T. et al., "Immunoregulatory Molecules (Lymphokines) Secreted from Human Monoclonal T Cell Lines".
Lakow, E. et al., Journal of Immunology, vol. 130, No. 1, pp. 169-172, (1983), "Human T Cell Hybridomas Specific for Epstein Barr Virus Infected B Lymphocytes".
DeFreitas, E. C. et al., Proc. Natl. Acad. Sci. U.S.A., vol. 79, pp. 6646-6650 (1982), "Antigen-Specific Human T-Cell Hybridomas with Helper Activity".
Greene, W. C. et al., Clinical Research, vol. 29, p. 368A (1981), "Production and Characteristics of Human T Cell Hybrids Exhibiting Suppressor Cell Activity".
Croce, C. M. et al., Nature, vol. 288, pp. 488-409 (1980), "Production of Human Hybridomas Secreting Antibodies to Measles Virus".
Grillot-Courvalin, C. et al., Nature, vol. 292, pp. 844-845 (1981), "Establishment of a Human T-Cell Hybrid Line with Suppressive Activity".
Okada, M. et al., Proc. Natl. Acad. Sci. U.S.A., vol. 78, No. 12, pp. 7717-7721 (1981), "Establishment and Characterization of Human T Hybrid Cells Secreting Immunoregulatory Molecules".
Köhler, G. et al., Nature, vol. 256, pp. 495-497 (1975), "Continuous Cultures of Fused Cells Secreting Antibody of Predefined Specificity".
Olsson, L. et al., Proc. Natl. Acad. Sciences U.S.A., vol. 77, No. 9, pp. 5429-5431 (1980), "Human-Human Hybridomas Producing Monoclonal Antibodies of Predefined Antigenic Specificity".
Levy, R. et al., Proc. Natl. Acad. Sci. U.S.A., vol. 75, No. 5, pp. 2411-2415 (1978), "Rescue of Immunoglobulin Secretion from Human Neoplastic Lymphoid Cells by Somatic Cell Hybridization".
Kappler, J. W. et al., J. Exp. Med., vol. 153, pp. 1198-1214 (1981), "Antigen-Inducible, H-2 Restricted, Interleukin-2-Producing T Cell Hybridomas".
Fox, R. M. et al., Cancer Research, vol. 40, pp. 1718-1721 (1980), "Mechanism of Deoxycytidine Rescue of Thymidine Toxicity in Human T-Leukenic Lymphocytes".

(List continued on next page.)

Primary Examiner—Margaret Moskowitz
Assistant Examiner—Jeff Kushan
Attorney, Agent, or Firm—Irell & Manella

[57] ABSTRACT

Human T-T hybridomas are made by fusing an azaserine-hypoxanthine (AH) sensitive T leukemia cell line, preferably the AH-sensitive mutant of the Jurkat leukemia line identified as J3R7, with normal T cells and culturing the fusion product in a selective AH medium. Stable, interleukin-2 (IL-2)-producing human T-T hybridomas were made by this process.

14 Claims, No Drawings

OTHER PUBLICATIONS

*Current Topics in Immunology and Microbiology,* vol. 81, pp. 27–36 (1978).
Kohler and Milstein, Nature, vol. 256:495 (1975).
Ollson and Kaplan, Proc. Natl. Acad. Sci., U.S.A., vol. 77:5429–5431 (1980).
Croce et al., Nature, vol. 288:488–409 (1980).
Levy and Dilley, Proc. Natl. Acad. Sci. U.S.A., vol. 75:4211–4215 (1978).
Kappler et al., J. Exp. Med., vol. 153:1198–1214 (1981).
Grillot–Courvalin et al., Nature, vol. 292:844 (1981).
Greene et al., Clin. Res., vol. 29:368A (1981).
Fox et al., Cancer Res., vol. 40:1718–1721 (1980).
Buttin et al., Curr Topics in Microbiol and Immunol, vol. 81:27–36 (1978).
Edwards et al., European J. Immunol., vol. 12(8):641–648 (1982).
Foung et al., Proc. Natl. Acad. Sci., U.S.A., vol. 79:7484–7488 (1982).
Lakow et al., The Journal of Immunology, vol. 130(1):169–172 (1983).

PROCESS FOR MAKING T CELL HYBRIDOMAS

REFERENCE TO GOVERNMENT GRANT

The invention described herein was made in the course of work under grant number CA24607 from the National Institutes of Health.

CROSS-REFERENCE TO RELATED APPLICATION

This application is a continuation of U.S. patent application Ser. No. 421,060, filed 22 Sept. 1982, now abandoned, which is a continuation-in-part of U.S. patent application Ser. No. 376,191, filed 7 May 1982, both of which are now abandoned.

DESCRIPTION

1. Technical Field

The invention is in the field of immunology. More particularly it is in the field of hybridoma technology and is directed to a process for producing T cell hybridomas and a T leukemia cell line used in the process.

2. Background Art

There are two main classes of lymphocytes involved in the immune system of humans and other vertebrates. Both classes of lymphocytes develop from hematopoietic stem cells. One is differentiated in the thymus and is thus called a "thymus-derived cell" or T cell. The second is differentiated in the bursa of Fabricius in avians and probably in the bone marrow of mammals and is called "bursa equivalent" or B cells.

B cells are involved in the humoral immune response. Under stimulation by an antigen the B cells differentiate into plasma cells that secrete antibody. B cells are found in peripheral blood, bone marrow, lymph, lymph node, spleen, tonsil, and thymus tissue.

T cells are subdivided into two major functional categories: regulatory and effector. The regulatory T cells may amplify (as helper cells) or suppress (as suppressor cells) the responses of other T cells or B cells. Effector T cells mediate cellular immune responses such as delayed hypersensitivity, foreign tissue rejection, and elimination of virus infected cells. T cells that are cytolytic are called "killer" cells. T cells are found in the same tissues as are B cells but usually in different proportions.

Hybridoma technology provides a technique for producing functional continuous T lymphocyte lines. This technology was discovered by Kohler and Milstein, *Nature* (1975) 256:495, and used by them to make hybrids between plasmacytomas and normal B cells to produce monoclonal antibodies. The technology involves fusing the two cell lines with a fusogen such as polyethylene glycol (PEG), selecting the hybridomas using a selective medium, typically hypoxanthine-aminopterin-thymidine (HAT) medium, expanding the hybrids, assaying the hybrids for the production of antibody and cloning those hybrids that make the desired antibody. Murine, human (Ollson and Kaplan (1980) *PNAS* 77:5429-5431 and Croce, et al (1980) *Nature* 288:488-409), and mixed species (Levy and Dilley (1978) *PNAS* 75:4211-4215) B cell hybridomas have been made using this technique.

While most of the hybridoma work done to date has involved B cells, the technology has also been used to make functional T cell hybridomas. Kappler, et al, *J Exp Med* (1981) 153:1198-1214 describe murine T cell hybridomas made by fusing an interleukin-2 (IL-2)-producing, HAT-sensitive murine T cell tumor line with normal murine T cell blasts enriched in H-2 antigen specific cells. The resulting hybrids could be induced to produce murine IL-2 by mitogen and/or antigens. Human T cell hybridomas have been described by Grillot-Courvalin, et al *Nature* (1981) 292:844; and Greene, et al, *Clin Res* (Apr., 1981) 29:368A. Grillot-Courvalin, et al disclose a T cell hybridoma made by hybridizing a HAT-sensitive T cell lymphoma with normal peripheral blood T cells. The Greene, et al article describes a suppressor T cell hybrid made by fusing a HAT-sensitive T leukemia cell line derived from a parent leukemia cell line designated CEM with peripheral blood lymphocytes enriched for suppressor T cells by treatment with concanavalin A (Con A).

Applicants are aware of prior work carried out at Leland Stanford Junior University Medical School by applicants Engleman and Foung in which a HAT-sensitive human T leukemia line was hybridized with a normal human T lymphocyte to produce human T cell hybridomas that were stable and produced IL-2 constitutively. Those hybridomas are the subject of commonly owned, U.S. patent application "IL-2 Producing Human T Cell Hybridoma", Ser. No. 413,758, filed 1 Sept. 1982 now abandoned.

A common problem among the above reported T cell fusions is the slow rate of growth in the resulting hybridomas. Applicants believe this is due at least partly to the growth inhibitory effect of thymidine in the HAT medium. Fox, et al, *Cancer Res* (1980) 40:1718-1721 report that the inhibitory effect of the thymidine could possibly be alleviated by the addition of deoxycytidine. Alternatives to HAT, such as a hypoxanthine-azaserine-thymidine medium (*Current Topics in Immunology and Microbiology* (1978) 81:27-36; and Edwards, P.A.W., et al, *European Journal of Immunology*, in press 1982) have been used in B cell fusions to allegedly increase the yield of hybrids.

A principal object of the present invention is to provide a process for making T cell hybridomas that avoids the use of a thymidine-containing selective medium. Another object of the invention is to provide a process for making T cell hybridomas that avoids the use of both aminopterin and thymidine in the selective medium, thereby permitting rapid growth and selection of hybrids. A further object is to provide a parent human T leukemia line that may be used in the invention process.

DISCLOSURE OF THE INVENTION

One aspect of the invention is a process for making a T cell hybridoma comprising:

(a) fusing an azaserine-hypoxanthine (AH) sensitive T leukemia cell line with normal T lymphocytes; and (b) culturing the product of step (a) in a selective azaserine-hypoxanthine medium.

Another aspect of the invention is a T leukemia cell line for use in the invention comprising an AH-sensitive mutant of the Jurkat human T leukemia line.

MODES FOR CARRYING OUT THE INVENTION

The principal differences between the invention process and the prior art processes that have been used to make T—T hybridomas are in the parent T leukemia line and the selective medium. The parent cells that are used in the process may be from any vertebrate species and may be from the same species or two different species in a given fusion. When the resulting hybridomas are to be used to make immunoregulatory agents or mediators of cellular immunity for human therapy, both fusion partners are preferably human. For convenience, the following disclosure describes embodiments of the invention that are particularly suitable for making human T—T hybridomas.

The fusion partners for making human T—T hybridomas are a human T leukemia line and normal (non-cancerous) human T lymphocytes. The T leukemia cell line is preferably a AH-sensitive mutant derived from the Jurkat human T leukemia cell line. The derivation of the Jurkat mutant was achieved by successively culturing parent Jurkat cells in media containing graded concentrations of 6-thioguanine. Prior to culturing, the parent cells may be optionally exposed to a mutagenic agent, eg alkylating agents such as ethylmethane-sulfonate, to increase the frequency of mutants. Surviving cells exhibit an inability to incorporate 6-thioguanine suggesting they are deficient in hypoxanthine-guanine phosphoribosyl transferase (HGPRT).

The parent leukemia cells may be cultivated in a flask in successive incubations using graded concentrations of 6-thioguanine. The initial 6-thioguanine concentration is preferably about $10^{-5}M$ and is progressively increased to about $10^{-4}M$. The total incubation time will typically be about 6 to about 12 weeks with the medium changed weekly. Accordingly, the number of incubations will usually be about 6 to 12. All incubations are carried out at physiological temperature (ca, 37° C.). Conventional nutrient media such as RPMI 1640 may be used in these cultivations supplemented with 10% fetal calf serum (FCS). Each incubation will usually take about one week, with viable cells being isolated before the succeeding incubation. Sufficient cells are used in each incubation to ensure the likelihood of obtaining viable cells at the end of the incubation period. The number of cells per flask (25 cc volume) will usually be about $10^7$. The fastest growing 6-thioguanine resistant clones are chosen for use in the fusion. Such clones will typically have a doubling time in the range of about 18 to 24 hr. If necessary, the clones may be expanded prior to fusion to provide a suitable supply of cells for the fusion.

Normal T lymphocytes from a variety of sources may be used in the fusion. Peripheral blood mononuclear leukocytes (PBL), spleen cells, thoracic duct cells, lymph node cells, bone marrow cells, and tonsil cells are examples of cells that may be used. For convenience, PBL are used rather than tissue cells. If hybridomas that produce immunoregulatory agents or mediators of cellular immunity are desired, the normal T lymphocytes may be cultured in a medium containing an inducer that induces production of such agents or mediators prior to fusion. The concentration of inducer in the medium will depend upon the particular inducer and the cell concentration. The cell concentration will usually be in the range of $5 \times 10^5/ml$ to $1 \times 10^6/ml$ and the inducer concentration will usually range between 0.05% to 1% by weight.

The AH-sensitive T leukemia cells and activated normal T lymphocytes are fused by combining the two in a medium containing a fusogen. Polyethylene glycol (PEG) of about 1500 daltons is a preferred fusogen, but other PEGs of molecular weight in the range of about 1000 to 4000 daltons or other fusogens may be used. The fusogen will normally be present at between about 40% and 60% (v/v), preferably at about 50% (v/v), in the medium. The medium is free of serum. The activated normal T cells and T leukemia cells will usually be combined at ratios of 2:1 to 1:10 with the total cells each being in the range of about $10^6$ to $5 \times 10^7$. A volume of 0.5 to 1 ml of fusion medium per $10^8$ cells is used. The cells are normally exposed to the fusion medium for about 5 to 10 minutes, preferably 7 to 8 minutes. A preferred fusion technique involves suspending the cells in the fusion medium followed by centrifugation of the cells while in contact with fusion medium. The fusion is carried out at room temperature, but with the fusogen prewarmed to 37° C.

Following the fusion the cells are separated from the fusion medium and washed repeatedly with fusogen-free medium to remove residual fusogen. The cells are then resuspended in the selective AH medium. The AH medium consists of a standard cell culture medium, such as RPMI or Dulbecco's medium, containing about 1 to about 20, preferably about 10, $\mu g$ azaserine per ml. The concentration of hypoxanthine in the medium is about 100 $\mu M$. The medium will also preferably contain serum, typically FCS, at a level of about 10% to 15% (v/v), an appropriate antibiotic such as penicillin/streptomycin and L-glutamine. Azaserine is a diazo analog of L-glutamine. Its main effect is an irreversible binding to various L-glutamine amino-transferases which are necessary in de novo purine biosynthesis. Its effect on pyrimidine synthesis is minimal and reversible with the addition of ademine. The use of azaserine in the selective medium avoids the necessity of using aminopterin which is an anti-folic acid antagonist and inhibits both purine and pyrimidine synthesis. Therefore, the use of azaserine eliminates the need for thymidine as an exogenous source of pyrimidine in the medium. This results in increased fusion efficiency and an increased rate of hybrid growth.

The cells are cultured in the AH medium in microtiter wells with an adherent mononuclear feeder cell layer that has been irradiated. The cells are cultured in the selective medium for a sufficient time to allow the unfused cells to die out. In this regard the unfused normal T lymphocytes, being nonmalignant, will have only a finite number of generations. Thus, after a certain period of time they will fail to reproduce. Unfused T leukemia cells will not be supported by the selective medium and will thus perish. Fused cells, on the other hand, will grow in the medium because they possess the immortality of the parent leukemia line and the normal T cell's ability to survive in the selective medium. The hybrid cells can use hypoxanthine to synthesize purine nucleotides. The selection will normally take about one to eight weeks, more usually about 2 weeks. By the end of the selection period, growth in wells containing viable hybrids should be visible.

After the selection the hybridoma culture media may be assayed for production of immunoregulatory agents or mediators if desired.

The success of the fusion and the stability of the resulting hybridomas may be verified by chromosomal analysis of the hybrids by conventional fixation and staining techniques. Hybrids will typically contain about 70 to about 90 chromosomes whereas the parent cells will contain substantially fewer chromosomes on the average (40–60). The hybridomas will typically have doubling times of about 1.5 to 4 days.

The hybridomas may be grown in vitro or in vivo by known techniques. Production of immunoregulatory agents or mediators may be enhanced by adding inducers to the culture medium. Care should be taken, however, against causing hyporesponsiveness by repeated induction. In vivo cell growth may be effected by introducing the hybridoma clones into a suitable immunodeficient host, such as nude mice or heavily irradiated mice. The clones will grow as ascites-producing tumors in such hosts. Compounds produced by the hybridomas may be isolated from the culture medium, ascites fluid, or serum, as the case may be, by known separation and purification techniques such as ammonium sulfate precipitation, dialysis, chromatography, and gel electrophoresis.

The following example demonstrates an embodiment of the invention for making T—T hybridomas that produce IL-2. This example is not intended to limit the invention in any manner.

T leukemia line

Cells from the Jurkat line (obtained from John Hansen, University of Washington at Seattle) were initially placed in RPMI 1640 containing $10^{-5}$M 6-thioguanine (6TG) and 10% FCS. After one week, the surviving cells were transferred to the same basic medium but containing $5 \times 10^{-5}$M 6TG. Over a 6 week period, the level of 6TG was increased to $2 \times 10^{-4}$M. All cultivations were carried out at 37° C. Cells were then cloned by limiting dilution at ½ cell/well in the $2 \times 10^{-4}$M 6TG-containing medium. One subclone, designated J3R7, that is 6TG-resistant was chosen for the fusion. A sample of the J3R7 T leukemia cell line was deposited at the American Type Culture Collection, 12301 Parklawn Drive, Rockville, Md 20852 on 2 Sept., 1982 and has been assigned the ATCC number CRL 8169.

Normal T lymphocytes

PBL were isolated from healthy human volunteers by Ficoll-Hypaque gradient centrifugation. The lymphocytes were stimulated with 1 μg/ml of phytohemagglutinin (PHA-P) in a 95% $O_2$/5% $CO_2$ atmosphere at 37° C. for 24 hr.

Fusion Procedure

The stimulated PBL at a concentration of $4 \times 10^7$ cells and the J3R7 line at a concentration of $4 \times 10^7$ cells were fused using 50% (v/v) 1500 dalton PEG in serum-free, RPMI 1640 solution. One cc of the PEG solution was added to the cell mixture over one minute. The resulting suspension was left at room temperature for one minute and then subjected to centrifugation at $500 \times g$ for 3 minutes. After 8 minutes the supernatant was suctioned off and the cell pellet was resuspended in RPMI 1640 over one minute, followed by an additional 6 cc of RPMI 1640 and 10% FCS solution. The suspension was then spun at $250 \times g$ for 10 minutes. The supernatant was suctioned off and the pellet was resuspended in 10 cc of RPMI 1640 and 10% FCS. The suspension was again spun at $250 \times g$ for 10 minutes. After these washings the cells were resuspended in RPMI 1640 medium containing 15% FCS, 25 mM Hepes buffer, 2 mM glutamine, 10 μg/ml azaserine, and 100 μM hypoxanthine. The cells were cultured in 24 well trays at a concentration of $10^6$ cells/well in 1 ml with a feeder layer of 200,000 adherent cells (irradiated 5000 rads) per well. The cultures were maintained at 37° C. in a humidified 95% air, 5% $CO_2$ atmosphere. After two weeks in culture growth was noted. After about one week the medium was changed to the same medium with hypoxanthine but without azaserine.

IL-2 Assay

One week after the medium was changed to medium not containing azaserine the presence of IL-2 was assayed by the procedure of Watson, et al, JEM (1979) 150:849. The supernatants from many of the wells had IL-2. Six IL-2-producing clones were subcloned by limiting dilution using ten, five and one cell/well. Cultures of the subclones exhibited stable, continuous growth and continuous production of IL-2.

Chromosome Analysis

Chromosome preparations of the subclones were performed according to standard techniques. Approximately $10^6$ cells per 1 cc are placed in RPMI 1640, 10% FCS and a final concentration of 0.5 μg/ml of vinblastine. After 3 hr of incubation in 95% $O_2$ and 5% $CO_2$ at 37° C., the cells are harvested by spinning at $250 \times g$ for 5 minutes. The cell pellet is then suspended is approximately 5 cc of a hypotonic solution (one part growth medium and two parts distilled water) for 10 minutes. The cells are again harvested by spinning at $250 \times g$ for 5 minutes and a fixative (three parts methyl alcohol and one part glacial acetic acid) is then added to each sample of about 1 cc fixative. The cells are washed in this fixative two times and resuspended with a few drops of the fixative and placed on a microscopic slide. The slide upon drying is stained with a Wright-Gimesa stain. The subclones contained about 70 to 90 chromosomes as compared to 40–50 chromosomes for the parent Jurkat cell line. Repeat chromosome analyses indicated that the subclones have stable karyotypes.

One of the hybridoma subclones has been designated J3R-All and a sample of the J3R-All IL-2 producing human T cell hybridoma line was deposited at the American Type Culture Collection, 12301 Parklawn Drive, Rockville Md. 20852 on 25 Aug. 1982 and has been assigned the ATCC number HB 8158.

Modifications of the above described modes for carrying out the invention that are obvious to those of ordinary skill in hybridoma technology, immunology, and/or related fields are intended to be within the scope of the following claims.

We claim:

1. A process for making a T cell hybridoma comprising:
   a. Fusing an azaserine-hypoxanthine sensitive human T leukemia cell line with normal human T cells; and
   b. culturing the product of step a. in a selective azaserine-hypoxanthine medium, wherein said human T leukemia cell line is a derived from the Jurkat human T cell line.

2. The process of claim 1 wherein the T cell hybridoma is a human T cell hybridoma, the T leukemia cell line is a human T leukemia line and the normal T cells are normal human T cells.

3. The process of claim 2 wherein the normal human T cells have been treated with an inducer that induces production of an immunoregulatory agent or a soluble mediator of cellular immunity.

4. The process of claim 3 wherein the inducer induces production of IL-2.

5. The process of claim 4 wherein the azaserine-hypoxanthine sensitive human T leukemia line has the identifying characteristics of the human T leukemia cell line ATCC number CRL 8169.

6. The process of claim 4 wherein the azaserine-hypoxanthine sensitive human T leukemia line is the J3R7 cell line.

7. The process of claim 1 wherein polyethylene glycol is used as a fusogen in step (a).

8. The process of claim 2 wherein the concentration of azaserine in the medium is about 1 to 20 $\mu$g/ml and the concentration of hypoxanthine in the medium is about 100 $\mu$M.

9. The process of claim 8 wherein the azaserine-hypoxanthine sensitive T leukemia cell line has the identifying characteristics of ATCC number CRL 8169.

10. The process of claim 8 wherein the azaserine-hypoxanthine sensitive T leukemia cells are cells of the Jurkat cell line.

11. An azaserine-hypoxanthine sensitive mutant of the Jurkat human T leukemia cell line and progeny thereof.

12. A human T leukemia cell line having all the identifying characteristics of ATCC number CRL 8169 and progeny thereof.

13. Jurkat human T leukemia cell line J3R7 and progeny thereof.

14. A method for the production of IL-2 comprising:
  c. culturing a hybridoma produced by the fusion of an azaserine-hypoxanthine sensitive human T cell leukemia cell line and a normal human T cell, wherein said human T leukemia cell line is derived from the Jurkat human T cell line, and wherein the cloning is carried out in the presence of an inducer which induces IL-2 production;
  d. detecting the presence of IL-2 in the supernatents of said cultured hybridomas, and
  e. isolating IL-2 from the supernatents of said hybridomas.

* * * * *